US012763219B2

(12) United States Patent
Amos-Binks et al.

(10) Patent No.: US 12,763,219 B2
(45) Date of Patent: Oct. 13, 2026

(54) CIRCULATORY SHOCK PREDICTION AND DIAGNOSIS MODEL

(71) Applicant: Applied Research Associates, Inc., Albuquerque, NM (US)

(72) Inventors: Adam Amos-Binks, Raleigh, NC (US); Christopher Nemeth, Evanston, IL (US); Gregory Rule, San Antonio, TX (US)

(73) Assignee: Applied Research Associates, Inc., Albuquerque, NM (US)

( * ) Notice: Subject to any disclaimer, the term of this patent is extended or adjusted under 35 U.S.C. 154(b) by 0 days.

(21) Appl. No.: 18/904,370

(22) Filed: Oct. 2, 2024

(65) Prior Publication Data

US 2026/0094719 A1 Apr. 2, 2026

(51) Int. Cl.

*G16H 50/30* (2018.01)
*G06N 20/00* (2019.01)
*G16H 50/20* (2018.01)

(52) U.S. Cl.

CPC ............. *G16H 50/30* (2018.01); *G06N 20/00* (2019.01); *G16H 50/20* (2018.01)

(58) Field of Classification Search

CPC ......... G16H 50/30; G16H 50/20; G06N 20/00
See application file for complete search history.

(56) References Cited

U.S. PATENT DOCUMENTS 8,262,579 B2 9/2012 Parlikar et al.
2007/0112275 A1 5/2007 Cooke et al.
2017/0053077 A1* 2/2017 Osypka ................ A61B 5/0816
(Continued)

FOREIGN PATENT DOCUMENTS

CA 3094294 A1 * 9/2019 ............. G16H 50/30
CN 110123277 A * 8/2019 ........... A61B 5/7267
(Continued)

OTHER PUBLICATIONS

Logothetis et al., "Predicting acute clinical deterioration with interpretable machine learning to support emergency care decision making," Scientific Reports | (2023) 13:13563 | https://doi.org/10.1038/s41598-023-40661-0. (Year: 2023).*
(Continued)

*Primary Examiner* — Jonathon A. Szumny
(74) *Attorney, Agent, or Firm* — Erise IP, P.A.

(57) ABSTRACT

Systems, methods, and computer-readable media for determining the probability of a patient developing shock. The method includes receiving, at a client device, a first set of vital sign measurements from the patient associated with a first time. The method includes determining, using a time-variant machine learning model, the probability of the patient developing shock based on the first set of vital sign measurements, the time-variant machine learning model having a first set of parameters associated with the first time. The method includes receiving, at the client device, a second set of vital sign measurements from the patient associated with a second time. The method includes updating, using the time-variant machine learning model, the probability of the patient developing shock based on the second set of vital sign measurements, the time-variant machine learning model having a second set of parameters associated with the second time.

19 Claims, 5 Drawing Sheets

(56) References Cited

U.S. PATENT DOCUMENTS

| | | | |
|---|---|---|---|
| 2017/0235917 | A1 | 8/2017 | Bighamian et al. |
| 2018/0032674 | A1* | 2/2018 | Asada ................ G02B 17/0663 |
| 2021/0022660 | A1* | 1/2021 | Quinn .................... G16H 40/67 |
| 2021/0052218 | A1 | 2/2021 | Quinn et al. |
| 2021/0059616 | A1* | 3/2021 | Abrol ................... A61B 5/7435 |
| 2021/0304855 | A1* | 9/2021 | Ansari ................... G16H 50/20 |
| 2021/0338174 | A1* | 11/2021 | Weffers-Albu ...... A61B 5/0035 |
| 2021/0391087 | A1* | 12/2021 | Gippetti ................. G16H 50/20 |
| 2022/0051796 | A1* | 2/2022 | Zhu .......................... G06N 7/01 |
| 2022/0233119 | A1* | 7/2022 | Shelton, IV ..... A61B 17/07207 |
| 2022/0301666 | A1 | 9/2022 | Shluzas et al. |
| 2022/0344013 | A1* | 10/2022 | Springs ................. G16H 50/20 |
| 2022/0384048 | A1* | 12/2022 | Gopalakrishnan ..... G16H 50/20 |
| 2022/0392605 | A1* | 12/2022 | Kurtz ..................... G16H 50/70 |
| 2023/0138432 | A1 | 5/2023 | Lee et al. |
| 2024/0079119 | A1* | 3/2024 | Kattan ................... G16H 50/20 |
| 2024/0260907 | A1* | 8/2024 | Centen ................... A61B 5/318 |
| 2025/0072819 | A1* | 3/2025 | Bajpai .................... G16H 50/70 |
| 2025/0152105 | A1* | 5/2025 | Bhatti ..................... G16H 50/20 |
| 2025/0292904 | A1* | 9/2025 | Wolber .................. G16H 50/20 |

FOREIGN PATENT DOCUMENTS

| | | | | | |
|---|---|---|---|---|---|
| CN | 114758786 | A | * | 7/2022 | ............ G06N 3/045 |
| KR | 20210050424 | A | * | 5/2021 | ............... G06N 3/08 |
| WO | WO-2022216220 | A1 | * | 10/2022 | ........... A61B 5/7267 |
| WO | WO-2024158742 | A1 | * | 8/2024 | ............. A61B 5/412 |
| WO | WO-2025058347 | A1 | * | 3/2025 | ............. G06N 20/00 |

OTHER PUBLICATIONS

Muralitharan et al., "Machine Learning-Based Early Warning Systems for Clinical Deterioration: Systematic Scoping Review," J Med Internet Res 2021 | vol. 23 | iss. 2 | e25187 | https://www.jmir.org/2021/2/e25187. (Year: 2021).*

Sun et al., "Continuous diagnosis and prognosis by controlling the update process of deep neural networks," Patterns 4, 100687 Feb. 10, 2023 ª 2023 The Author(s). https://doi.org/10.1016/j.patter.2023.100687. (Year: 2023).*

Perng et al., "Mortality Prediction of Septic Patients in the Emergency Department Based on Machine Learning," J. Clin. Med. 2019, 8, 1906; doi:10.3390/jcm8111906. (Year: 2019).*

Alshwaheen et al., "A Novel and Reliable Framework of Patient Deterioration Prediction in Intensive Care Unit Based on Long Short-Term Memory-Recurrent Neural Network," IEEE Access, date of publication Dec. 24, 2020, Digital Object Identifier 10.1109/ACCESS.2020.3047186. (Year: 2020).*

Morid et al., "Time Series Prediction Using Deep Learning Methods in Healthcare," ACM Transactions on Management Information Systems, vol. 14, No. 1, Article 2. Publication date: Jan. 2023; https://doi.org/10.1145/3531326. (Year: 2023).*

Jalaja et al., "Contactless face video based vital signs detection framework for continuous health monitoring using feature optimization and hybrid neural network," Biotechnol Bioeng. 2024;121:1190-1214; DOI: 10.1002/bit.28644. (Year: 2023).*

Pinevich, Y., et al, Machine Learning Algorithms to Identify and Differentiate Shock. Mayo Clinic Young Investigator Research Symposium. Rochester, MN (2020).

Amos-Binks, A., et al, Algorithms to Identify and Differentiate Shock in Combat Casualties. American Medical Informatics Association. Chicago, (May 2020).

Desautels, Thomas PhD, et al, Prediction of Sepsis in the Intensive Care Unit With Minimal Electronic Health Record Data: A Machine Learning Approach, JMIR Med Inform.Jul.-Sep. 2016; 4(3): e28, pp. 1-30, https://www.ncbi.nlm.nih.gov/pmc/articles/PMC5065680/?report=printable.

Amos-Binks, et al, Using EHR data in the development of machine learning models for shock identification and differentiation. Military Healthcare Research Symposium (MHSRS). Kissimmee, FL, (2019).

Nemeth, C., et al, Decision Support for Prolonged, and Tactical Combat Casualty Care. Proceedings of the 10th International Conference on Design, User Experience, and Usability. Washington, (2021).

Nemeth, C., et al, Evaluation Results for Medic and Clinician Decision Support Prototype with ML Shock Prediction. Military Health System Research Symposium. Kissimmee, FL, (2021).

Nemeth, C., et al, Real Time Battlefield Casualty Care Decision Support. (Jul. 2022). Proceedings of the Applied Human Factors and Ergonomics Conference. New York.

Nemeth, C., et al, Tactical Combat Casualty Care Decision Support for Medics, Battalion Aid Station and Field Hospital Clinicians. Military Healthcare Research Symposium (MHSRS). Kissimmee, FL, (2019).

Nemeth, C., et al, Training and Decision Support for Battlefield Trauma Care. Proceedings of the Systems Man and Cybernetics Society 2020 International Conference. Institute of Electrical and Electronic Engineers. Toronto (Oct. 2020).

Nemeth, C., et al, Trauma care decision support under fire. Proceedings of the Systems Man and Cybernetics Society 2019 International Conference. Institute of Electrical and Electronic Engineers. Bari, IT, (Oct. 2019).

Pinevich, Y., et al, Algorithms to Identify and Differentiate Shock in Combat Casualties. AMIA 2020 Virtual Clinical Informatics Conference. (May 19-21, 2020).

Pinevich, Y., et al, Development of a machine learning model for early shock detection. Critical Care Medicine.48(1):439, (Jan. 2020).

Pinevich, Yuliya, et al. "Validation of a Machine Learning Model for Early Shock Detection" in: Military Medicine, vol. 187, S1/2, pp. 82-88, 2022.

Pinevich, Y., et al, Process for development of a machine learning model for shock differentiation using electronic health record (EHR) data. Mayo Clinic 21st Annual Quality Conference. Rochester, MN, (2019).

Pinevich, Y., et al, Sensitivity Analysis of Input Variables of Shock Detection Model. AMIA Annual Symposium. 1877. Chicago, (Nov. 2020).

Nemeth, Christopher, et al. "TCCC Decision Support With Machine Learning Prediction of Hemorrhage Risk, Shock Probability" in: Military Medicine, vol. 188, S6: pp. 659-665, 2023.

Nemeth, Christopher, et al. "Decision Support for Tactical Combat Casualty Care Using Machine Learning to Detect Shock" in: Military Medicine, vol. 186, S1: pp. 273-280, 2023.

Pinevich, Y., et al, Development of a Machine Learning Model for Shock Differentiation. Society for Critical Care Medicine (2020).

Hyland, Stephanie L., et al, Early prediction of circulatory failure in the intensive care unit using machine learning, Nature Medicine, vol. 26, Mar. 2020, pp. 364-391, www.nature.com/naturemedicine.

PCT Patent Application PCT/US2025/47722 International Search Report and Written Opinion of the International Searching Authority issued Feb. 4, 2026.

* cited by examiner

CIRCULATORY SHOCK PREDICTION AND DIAGNOSIS MODEL

BACKGROUND

1. Field

Embodiments of the present disclosure relate to predicting shock in patients. More specifically, embodiments of the present disclosure relate to systems and methods utilizing machine learning for determining the probability and onset of shock.

2. Related Art

Shock (e.g., circulatory shock) is a condition that occurs when there is inadequate blood flow throughout the body. It can result in organ failure, permanent disability, or even death to those who develop it. The risks posed by shock are time dependent—the more time that goes on without treatment, the more lethal shock becomes. Thus, early prediction, detection, monitoring, and treatment of shock may significantly decrease the likelihood of serious side effects and even death. However, many challenges arise with advanced prediction of shock.

First, shock is often not readily apparent to the naked eye; instead, medical professionals may rely on laboratory tests that measure biological markers (e.g., lactate levels, etc.) to indicate the onset of shock. Such tests may include rule-based scoring systems and data-driven models. Current rule-based systems are often not precise enough due to their broad characterizations of a patient's risk of circulatory failure. On the other hand, current data-driven models may be more accurate but often require equipment unavailable outside of a hospital setting. For example, current data-driven models may rely on laboratory tests that are not practical in austere environments, such as in post-natural disaster and military battlefield situations, due to refrigeration requirements. Lastly, in many settings, the person tasked with early diagnosis and treatment of shock may not have the expertise needed to make proper diagnoses using currently available shock diagnostic methods, such as experience-based judgment calls. As such, systems and methods are desired to determine the probability or the onset of shock using readily available patient information.

SUMMARY

In some aspects, the techniques described herein relate to one or more non-transitory computer-readable media including computer-executable instructions that, when executed by at least one processor, perform a method of determining a probability of a patient going into shock, the method including: receiving, at a client device, a first set of vital sign measurements from the patient associated with a first time; determining, using a time-variant machine learning model, the probability of the patient going into shock based on the first set of vital sign measurements, the time-variant machine learning model having a first set of parameters associated with the first time; receiving, at the client device, a second set of vital sign measurements from the patient associated with a second time; and updating, using the time-variant machine learning model, the probability of the patient going into shock based on the second set of vital sign measurements, the time-variant machine learning model having a second set of parameters associated with the second time, the second set of parameters differing from the first set of parameters.

In some aspects, the techniques described herein relate to one or more non-transitory computer-readable media, wherein the method further includes: determining, using a body sensor associated with the patient, the first set of vital sign measurements.

In some aspects, the techniques described herein relate to one or more non-transitory computer-readable media, wherein the body sensor includes at least one of an armband, wristwatch, or chest strap.

In some aspects, the techniques described herein relate to one or more non-transitory computer-readable media, wherein determining the first set of vital sign measurements includes: evaluating, using a computer vision model, a set of image data associated with the patient, wherein the body sensor includes at least one of a camera or a camcorder.

In some aspects, the techniques described herein relate to one or more non-transitory computer-readable media, wherein the time-variant machine learning model is trained using a training data set including ICD data.

In some aspects, the techniques described herein relate to one or more non-transitory computer-readable media, wherein a diagnosis buffer is associated with the ICD data such that a delay in input of the ICD data relative to patient shock development is accounted for.

In some aspects, the techniques described herein relate to one or more non-transitory computer-readable media, wherein the time-variant machine learning model is trained using a training data set cleansed to remove at least one of duplicate data, polytrauma patient data, or re-admitted patient data.

In some aspects, the techniques described herein relate to a method for determining a probability of a patient going into shock, the method including: receiving, at a client device, a first set of vital sign measurements from the patient associated with a first time; determining, using a time-variant machine learning model, the probability that the patient will go into shock within a predetermined time period based on the first set of vital sign measurements, the time-variant machine learning model having a first set of parameters associated with the first time; receiving, at the client device, a second set of vital sign measurements from the patient associated with a second time; updating, using the time-variant machine learning model, the probability that the patient will go into shock within the predetermined time period based on the first set of vital sign measurements and the second set of vital sign measurements, the time-variant machine learning model having a second set of parameters associated with the second time, the second set of parameters differing from the first set of parameters; receiving, at the client device, a third set of vital sign measurements from the patient associated with a third time; and updating, using the time-variant machine learning model, the probability that the patient will go into shock within the predetermined time period based on the first set of vital sign measurements, the second set of vital sign measurements, and the third set of vital sign measurements, the time-variant machine learning model having a third set of parameters associated with the third time, the third set of parameters differing from the first set of parameters and the second set of parameters.

In some aspects, the techniques described herein relate to a method, further including: measuring the first set of vital sign measurements associated with the patient, including: capturing a set of image data associated with the patient using a recording device; and determining, by inputting the set of image data into a computer vision model, the first set of vital sign measurements.

In some aspects, the techniques described herein relate to a method, wherein the first time and the second time are relative to an initial time, the initial time being a beginning of a monitoring period of the patient.

In some aspects, the techniques described herein relate to a method, wherein the first set of parameters is determined based on a subset of training data associated with a delay time, the delay time relative to a length of time since a historical monitoring period began.

In some aspects, the techniques described herein relate to a method, wherein the predetermined time period is 90 minutes.

In some aspects, the techniques described herein relate to a method, wherein the time-variant machine learning model is trained using a training data set including historical vital sign measurements over a plurality of time periods and a set of physiological relationships between the historical vital sign measurements during the plurality of time periods.

In some aspects, the techniques described herein relate to a method, wherein the first set of vital sign measurements and the second set of vital sign measurements each include a heart rate measurement, a diastolic blood pressure measurement, a systolic blood pressure measurement, a temperature measurement, a respiratory rate measurement, and a peripheral capillary oxygen saturation (SpO2) measurement.

In some aspects, the techniques described herein relate to a system for determining a probability of a patient going into shock, the system including: a body sensor for measuring a plurality of vital sign measurements associated with the patient; a time-variable machine learning model for determining the probability of the patient going into shock; and one or more non-transitory computer-readable media including computer-executable instructions that, when executed by at least one processor, perform a method of determining the probability of the patient going into shock, the method including: receiving a first set of vital sign measurements from the plurality of vital sign measurements associated with a first time; determining, using a time-variant machine learning model, the probability of the patient going into shock based on the first set of vital sign measurements, the time-variant machine learning model having a first set of parameters associated with the first time; receiving a second set of vital sign measurements from the plurality of vital sign measurements associated with a second time; and updating, using the time-variant machine learning model, the probability of the patient going into shock based on the second set of vital sign measurements, the time-variant machine learning model having a second set of parameters associated with the second time, the second set of parameters differing from the first set of parameters.

In some aspects, the techniques described herein relate to a system, wherein the time-variant machine learning model is trained to determine the probability of shock for the patient when the patient is in an austere environment.

In some aspects, the techniques described herein relate to a system, wherein the method further includes: storing the first set of vital sign measurements and the probability of shock occurring for retraining the time-variant machine learning model.

In some aspects, the techniques described herein relate to a system, wherein the body sensor is attached to the patient and transmits signals to a client device associated with a user, the client device running the time-variant machine learning model.

In some aspects, the techniques described herein relate to a system, wherein the time-variant machine learning model is agnostic to shock types such that the time-variant machine learning model determines the probability of a plurality of shock types occurring.

In some aspects, the techniques described herein relate to a system, further including: a client device configured to present a set of vital sign measurements associated with the patient and the probability of the patient going into shock to a user, wherein the probability of the patient going into shock is presented to the user when the probability exceeds a predetermined threshold.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present disclosure will be apparent from the following detailed description of the embodiments and the accompanying drawing figures.

BRIEF DESCRIPTION OF THE DRAWING FIGURES

Embodiments of the present disclosure are described in detail below with reference to the attached drawing figures, wherein.

Figure 1:
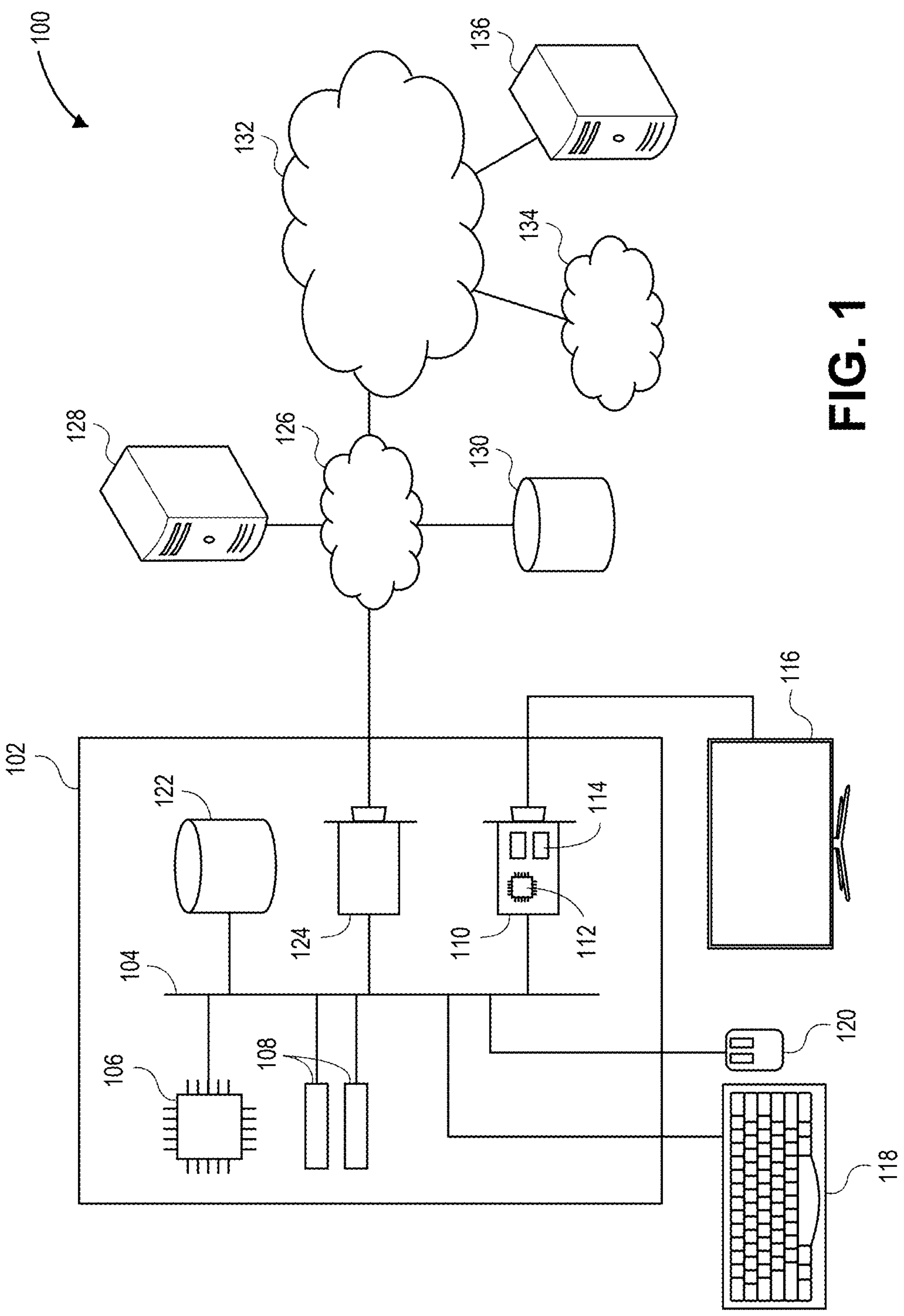
FIG. 1 depicts an exemplary hardware system, in accordance with embodiments of the invention.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The following detailed description references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized, and changes can be made without departing from the scope of the present disclosure. The following detailed description is, therefore, not to be taken in a limiting sense. The scope of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Generally, embodiments of the present disclosure relate to systems and methods for determining the occurrence of and/or the onset of shock for a patient based on information gathered from the patient. In some embodiments, vital sign information from a patient is gathered by a body sensor or a collection of body sensors. The vital sign information may then be transmitted to a client device. The client device may be used to display the vital sign information of a patient to a user, who may be, for example, the patient or a third party. The client device may also interface with a time-variant machine learning model to analyze the vital sign information for determining if the patient is developing shock. The time-variant machine learning model determines the probability of shock occurring within a predetermined amount of time, given the vital sign measurements of a patient at a time relative to an initial time (e.g., when the monitoring of a patient began, when the patient became symptomatic, etc.). As stated above, the machine learning model is time-variant, meaning the parameters (e.g., weights) associated with the features of the machine learning model vary depending on the collection time associated with the feature values relative to an initial time and on previous feature values collected. For example, a high heart rate may have a greater impact on the prognosis of shock at a time after the initial time than at the initial time, and may similarly have a greater impact on the prognosis of shock after a low blood pressure state has been detected, even if that low blood pressure state has been resolved. Upon determining if a patient is in shock, is going into shock, or is likely to imminently go into shock, a third party may be able to deliver medical treatment.

FIG. 1 illustrates an exemplary hardware platform relating to some embodiments of the present disclosure. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments, no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removably attached.

Such non-transitory computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth®, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is, in turn, connected to Internet 132, which connects many networks such as local network 126, remote network 134, or directly attached computers such as computer 136. In some embodiments, computer 102 can itself be directly connected to Internet 132.

Figure 2:
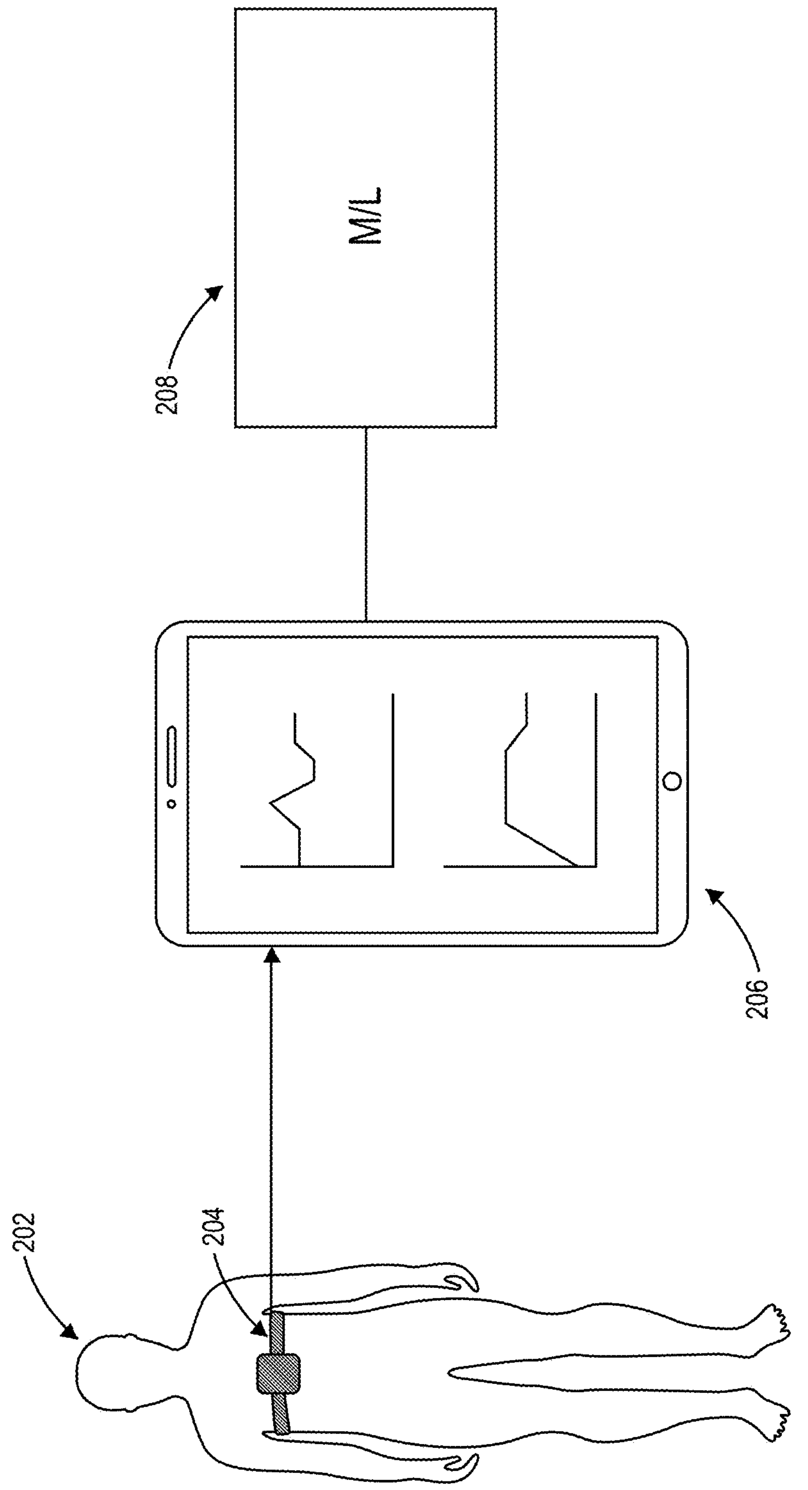
FIG. 2 depicts an exemplary system for diagnosing shock, in accordance with embodiments of the invention.

Continuing on, FIG. 2 illustrates an exemplary system for diagnosing shock relating to some embodiments of the present disclosure. Broadly, shock diagnosis system 200 may measure (including in real time) the vital signs of patient 202 and the occurrence and/or likelihood (e.g., probability) of occurrence of shock associated with the vital sign measurements. In some embodiments, shock diagnosis system 200 may provide information indicative of whether patient 202 has developed clinical shock and/or will develop clinical shock, such as a binary value (e.g., yes or no). In some embodiments, shock diagnosis system 200 may indicate with a percentage and/or a probability whether patient 202 has developed clinical shock and/or will develop clinical shock.

In some embodiments, shock diagnosis system 200 may be agnostic to the different types of shock. As such, shock diagnosis system 200 may be a system capable of predicting the probability and/or presence of all types of shock. In other embodiments, shock diagnosis system 200 may be tailored to one or more types of shock, such as cardiogenic shock, hypovolemic shock, anaphylactic shock, obstructive shock, and septic shock. In such embodiments, shock diagnosis system 200 may measure and evaluate biological markers relating to a specific type of shock. Such a system may be useful in environments in which the probability of a specific type of shock occurring is much greater than the probability of other types of shock occurring.

In some embodiments, shock diagnosis system 200 measures vital signs of patient 202 using body sensor 204. Body sensor 204 may capture any number of body vital signs, body processes, and biological responses. In some embodiments, body sensor 204 captures heart rate, diastolic blood pressure, systolic blood pressure, temperature, respiratory rate, and peripheral capillary oxygen saturation (SpO2). As such, body sensor 204 may contain any number of probes and sensors to measure the desired vital signs. For example, body sensor 204 may include a thermometer, a finger cuff, a pulse oximeter, an arm cuff, a chest band device, a heart rate monitor, and similar devices.

In some embodiments, body sensor 204 may include a camera, camcorder, recording device, etc., for capturing video and/or image data of patient 202. Accordingly, the video and/or image data may be analyzed to identify any number of characteristics of patient 202, including the vital signs of patient 202. Any method now known or later developed may be utilized to analyze the image data to determine the vital signs of patient 202, including, but not limited to, computer vision models. For example, a set of image data may be inputted into one or more computer vision models to determine the vital signs of patient 202, such as the heart rate of patient 202.

Body sensor 204 may be a singular sensor device or a collection of sensors. For example, body sensor 204 may be a wearable device made up of interconnected sensors, such as a chest-strapped device, finger-worn device, or a wristband device, where each sensor transmits measurements back to a singular location for transmittal to monitoring device 206. For another example, body sensor 204 may be a series of independently operating sensors that each transmit measurement data to monitoring device 206.

In some embodiments, body sensor 204 transmits vital sign information to monitoring device 206, such as via a transmitter device. Monitoring device 206 may be any device now known or later developed, including, but not limited to, a cellular device, a computer, a tablet device, a desktop computer, a laptop computer, a watch device, and similar devices. In some embodiments, the functionality described below with respect to monitoring device 206 may be contained in an application, such as a web application.

At a high level, monitoring device 206 may receive the vital sign information (such as via a receiver device) and display the vital sign information associated with patient 202. This may allow a user of monitoring device 206 to monitor patient 202 for any number of purposes, such as to assess the need for medical treatment. Generally, the user of monitoring device 206 may be any entity monitoring the condition of patient 202, including, but not limited to, a physician, a nurse, a civilian, military personnel, patient 202, a computer system, and the like.

Monitoring device 206 may display a range of information, including, but not limited to, the vital sign measurements of patient 202, demographical information of patient 202, indicators of shock, the probability of patient 202 developing shock, and the like. In some embodiments, monitoring device 206 may present a user with the numerical value associated with a vital sign at a given time, such as, "body temperature: 98.6° F." Values may be identified as being within or outside clinically normal ranges, where clinically normal ranges are predetermined ranges in which values are deemed normal and/or unconcerning by medical professionals. For example, if a clinically normal range for body temperature is set to be 97.00° F.-99.00° F., monitoring device 206 may provide information indicative of a measured body temperature of 99.15° F.

In some embodiments, as stated above, the vital signs may be displayed on monitoring device 206 as a function of time (e.g., in a graph). By providing a user with vital signs as a function of time, the user may be visually see the condition of patient 202 over a period of time to determine trends in said condition. For example, a user may be able to visually see that the heart rate, blood pressure, and temperature of patient 202 have increased in the last 10 minutes. By providing visual indicators of the vital sign measurements of patient 202, duration of vital sign measurements, and variation of vital sign measurements, a user may be able to determine that patient 202 has a medical condition that requires the administration of treatment. In some embodiments, monitoring device 206 may display a prediction and/or information indicative of the probability of patient 202 going into shock. For example, monitoring device 206 may display, "Likelihood of Shock: 95%." In some embodiments, monitoring device 206 may alert the user that patient 202 may develop shock or is experiencing shock, such as through a sound, a visual element, a color, a message, a push notification, haptic feedback, or a graph.

In some embodiments, monitoring device 206 may interface with time-variant machine learning model 208 to determine the probability of patient 202 developing shock based on the vital sign measurements received from body sensor 204. Broadly, time-variant machine learning model 208 determines whether shock will occur and/or the probability of shock occurring within a predetermined period of time. For example, time-variant machine learning model 208 may determine the probability of shock occurring within a 90-minute timeframe. For another example, time-variant machine learning model 208 may determine the probability of shock occurring in a timeframe greater than and/or shorter than 90 minutes. Determining the probability of shock developing within a predetermined time period proves advantageous, as it may allow for treatments and/or therapies to be administered to prevent shock before shock is predicted to occur. In some embodiments, time-variant machine learning model 208 may be able to predict the onset of shock before a human may be able to diagnose shock. For example, time-variant machine learning model 208 may be able to determine a trend occurring in the vital signs of patient 202 before a user is able to recognize the same trend based on the medical experience of the user.

Time-variant machine learning model 208 may utilize any type of machine learning now known or later developed including, but not limited to, gradient boosting, random forests, logistic regression, linear regression, linear discriminant analysis, classification and regression trees, naive Bayes, K-nearest neighbors, support vector machines, adaptive boosting, non-linear models, neural networks, transformers, and similar machine learning models. As discussed below with respect to FIG. 3, time-variant machine learning model 208 may be trained on any suitable data set including, but not limited to, historical patient data, intensive care unit (ICU) data, ICD codes, physiological relationship information, and the like.

As discussed above, time-variant machine learning model 208 is time-variant, meaning the parameters (e.g., weights) associated with the features of time-variant machine learning model 208 vary depending on the collection time associated with the feature values relative to an initial time. For example, the parameters used by time-variant machine learning model 208 at a particular time to determine the probability of shock may be dependent on how particular vital signs relate to each other over time and at said particular time. For example, at time A, the relationship of the values of vital sign A and vital sign B may not be indicative of shock and therefore may not be given any weight by machine learning model 208 in determining the probability of shock at time A. However, at time B, the relationship of the values of vital sign A and vital sign B may be correlated with the development of shock and, therefore, be given an increased weight by time-variant machine learning model 208 in determining the probability of shock at time B as opposed to at time A.

The parameters used by time-variant machine learning model 208 may change according to a predetermined interval. For example, the parameters used by time-variant machine learning model 208 may be modified every 10 minutes of a monitoring period such that time-variant machine learning model 208 utilizes a first set of parameters to determine shock during a first 10-minute period and a second set of parameters to determine shock during a second 10-minute period following the first 10-minute period. Time-variant machine learning model 208 is discussed further below as it relates to time-variant machine learning model 308 depicted in FIG. 3.

Figure 3:
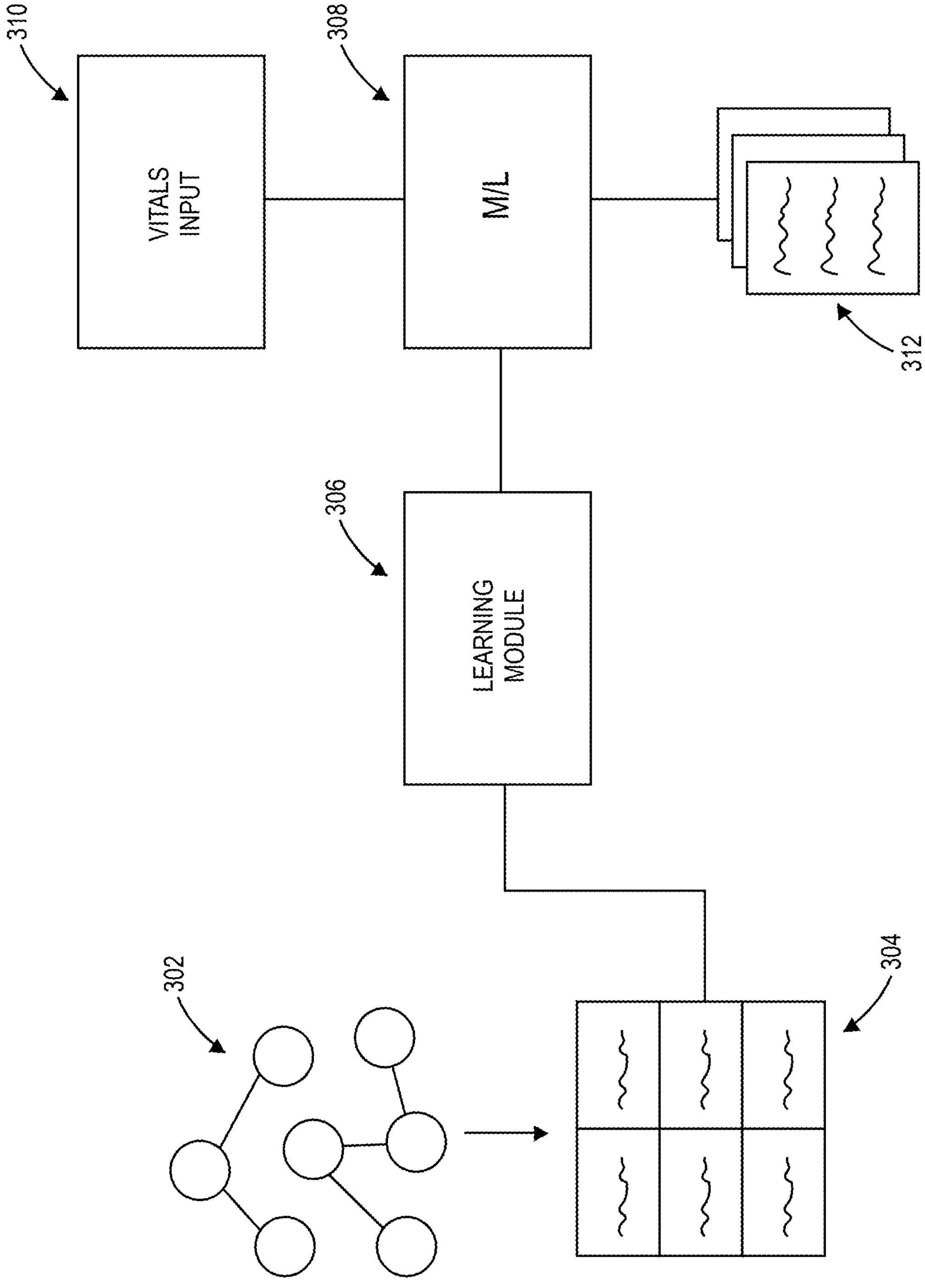
FIG. 3 depicts an exemplary system for training a machine learning model, in accordance with embodiments of the invention.

FIG. 3 illustrates an exemplary system for training a machine learning model relating to some embodiments of the present disclosure. At a high level, training system 300 trains a machine learning model to receive an input of vital sign measurements associated with a time and determine the probability of shock based on the vital sign measurements. In some embodiments, training system 300 may include physiological relationships 302, vital sign training data 304, learning module 306, time-variant machine learning model 308 (generally relating to time-variant machine learning model 208 depicted in FIG. 2), vital sign measurements 310, and shock prediction 312.

Generally, various biological processes of the human body are interconnected and interrelated. For example, heart rate and blood pressure are related, such that an increase in heart rate may increase blood pressure and vice versa. As such, learning module 306 may utilize vital sign training data 304, including physiological relationships 302, to train time-variant machine learning model 308. Physiological relationships 302 may include information indicative of the interconnection and interrelation of vital sign measurements. For example, physiological relationships 302 may include information indicative of the relationship between respiratory rate and oxygen level, such as when the respiratory rate of a patient decreases, the patient's oxygen level also decreases. Thus, by training time-variant machine learning model 308 using both vital sign training data 304 and physiological relationships 302, time-variant machine learning model 308 may analyze each vital sign measurement both independently and in relation to other vital sign measurements for determining the probability of shock occurring.

As mentioned above, learning module 306 may utilize vital sign training data 304 to train time-variant machine learning model 308. At a high level, vital sign training data 304 may include vital sign measurements as they relate to shock and the development of shock. Relevant measurements may include but are not limited to, heart rate, diastolic blood pressure, systolic blood pressure, temperature, respiratory rate, peripheral capillary oxygen saturation (SpO2), the ratio of partial pressure of arterial oxygen (PaO2) to the fraction of inspired oxygen (FiO2) (P/F ratio), urinary output, mental status, coagulation, bilirubin levels, and similar information. In some embodiments, vital sign training data 304 may extend beyond vital sign measurements to other relevant information including, but not limited to, laboratory/test results of patients, physically administered treatments, and the like. As such, vital sign training data 304 may be from any number of data sets now known or later developed, including, but not limited to, intensive-care unit data, clinical expertise data, electronic hospital records, and the like.

Vital sign training data 304 may be in any format now known or later developed, including, but not limited to, numerical values, binary values, natural language, auditory files, written text, imagery, video, and the like. In some embodiments, vital sign training data 304 may be specific to a particular treatment environment. For example, vital sign training data 304 may be limited to data gathered in a hospital setting. For another example, vital sign training data 304 may be limited to data gathered in an active field setting, such as on a battlefield. In some embodiments, vital sign training data 304 may include only vital signs that are able to be measured for a given environment. For example, vital sign training data 304 may include a broader range of information when time-variant machine learning model 308 is tailored for use in a hospital setting rather than in a battlefield setting. However, it is noted herein that time-variant machine learning model 308 need not be tailored for a particular environment and can instead be equipped for deployment in any and all types of environments.

In some embodiments, vital sign training data 304 may be informed and/or derived from ICD data. Generally, ICD data may be linked to the diagnoses and treatments administered by medical professionals while in a hospital setting. As such, ICD data may include information on when a patient may have been diagnosed with a particular disease and what the patient's vital signs were before diagnosis. Therefore, ICD data may inform a machine learning model on what vital sign patterns may result in diagnosable shock. The ICD data may include information on any number of items, including, but not limited to, demographic information, collected vital signs, time stamps for treatment, time stamps for diagnoses, treatment type, diagnosis type, charted information, and similar pieces of information. For example, ICD data may include a binary value (e.g., yes or no, 1 or 0) indicating whether or not a patient was treated for shock during a hospital visit. In some embodiments, when ICD data has been used to train time-variant machine learning model 308, vital sign training data 304 may include information indicative of a diagnosis buffer to account for potential delay in assigning ICD data from when a patient actually developed shock. The diagnosis buffer may refer to a period of time in which a patient likely was in shock before ICD data indicative of shock was recorded. Accordingly, the diagnosis buffer may prevent time-variant machine learning model 308 from inaccurately determining the probability of shock for a given time relative to an initial time based on an overestimation of the time necessary to develop shock learned from ICD data without a corresponding diagnosis buffer.

In some embodiments, vital sign training data 304 may be filtered (such as by learning module 306) before vital sign training data 304 is applied to training time-variant machine learning model 308. Broadly, vital sign training data 304 may contain spurious data that will make time-variant machine learning model 308 less accurate in determining the probability of shock. For example, vital sign training data 304 may contain vital sign training data 304 from patients who were treated for shock (such as being put on a ventilator). For another example, vital sign training data 304 may contain patients experiencing polytrauma such that vital sign trends may not be fully attributable to the development of shock. For another example, vital sign training data 304 may contain patients who were monitored for varying lengths of time, including significantly shorter periods of time before treatment was administered. As such, learning module 306 may filter vital sign training data 304 so as to remove spurious data (such as the data types indicated above) that may lead to inaccurate determinations of shock. Removing spurious data may result in vital sign training data 304 including data that substantially resembles the scenarios in which time-variant machine learning model 308 may be used to predict shock.

To illustrate, ICD data may be analyzed, cleaned, and/or filtered before being used for training time-variant machine learning model 308. Filtering the ICD data may remove various forms of error associated with ICD data. For example, ICD data may signify the time in which treatment was administered; not necessarily when a patient developed diagnosable shock. Therefore, as mentioned above, a buffer may be applied to the ICD data to account for the fact that shock may have occurred before the ICD data says it was treated. Other examples of potential errors include multiple admissions, incorrect input, duplicate input, and the like. Therefore, in order to preserve the accuracy of time-variant machine learning model 208 in detecting shock, ICD data (as well as any other data) may be analyzed, filtered, and cleaned.

In some embodiments, vital sign training data 304 may include a ground truth data set for validating the operation of time-variant machine learning model 208. The ground truth data set may be based on physicians administering treatment in real-life shock scenarios. For example, the ground truth data set may define the time in which a physician-administered treatment (for example, as shown through ICD data). As such, the ground truth data set may define a time that can be considered the time in which shock has occurred. Thus, the vital signs of a patient taken before the shock occurred may be considered biological markers leading up to the occurrence of shock for purposes of training a machine learning model.

Continuing on, in some embodiments, learning module 306 may train time-variant machine learning model 308 using vital sign training data 304. Learning module 306 may train time-variant machine learning model 308 to determine the probability of shock occurring in a predetermined time. For example, learning module 306 may train time-variant machine learning model 308 to determine the probability of shock occurring for a given patient in the next 90 minutes. Time-variant machine learning model 308 may be trained by learning module 306

Generally, as discussed above, the observable vital sign measurements for shock change over the window in which a patient develops shock. For example, the vital sign measurements observed 15 minutes before a patient goes into shock may be drastically different than the vital sign measurements observed 30 minutes before a patient goes into shock. As such, in some embodiments, learning module 306 may train time-variant machine learning model 308 such that time-variant machine learning model 308 changes the way in which it evaluates the probability of shock for a given set of vital signs depending on the time (e.g., time-variant machine learning model 308 is time variant/dependent). Specifically, learning module 306 may train time-variant machine learning model 308 to utilize differing sets of parameters depending on the time associated with vital sign measurements 310. In some embodiments, time-variant machine learning model 308 is trained to change the parameters used by time-variant machine learning model 308 to determine shock at a predetermined time interval, such as every 5 minutes. In some embodiments, time-variant machine learning model 308 is trained to change every time a new vital sign measurement is inputted into the model.

In some embodiments, in order to train time-variant machine learning model 308 to utilize differing parameters depending on the time associated with vital sign measurements 310, times may be associated with the various data points of vital sign training data 304. The times associated with vital sign training data 304 may be relative to any number of initial points in time, including, but not limited to, the time in which the monitoring of a patient began, the time in which a patient was admitted to a medical facility, the time in which a patient was treated for shock, or the time in which a patient was diagnosed with shock. Accordingly, vital sign measurements 310 may be evaluated by time-variant machine learning model 308 using parameters determined using a subset of vital sign training data 304 that occurred at a substantially similar time to that of vital sign measurements 310. For example, vital sign measurements 310 taken 10 minutes after the monitoring of a patient began may be evaluated by time-variant machine learning model 308 using parameters learned by time-variant machine learning model 308 given a subset of vital sign measurements 310 that relates to historical patient data gathered 10 minutes after the monitoring for a plurality of patients began.

Figure 4:
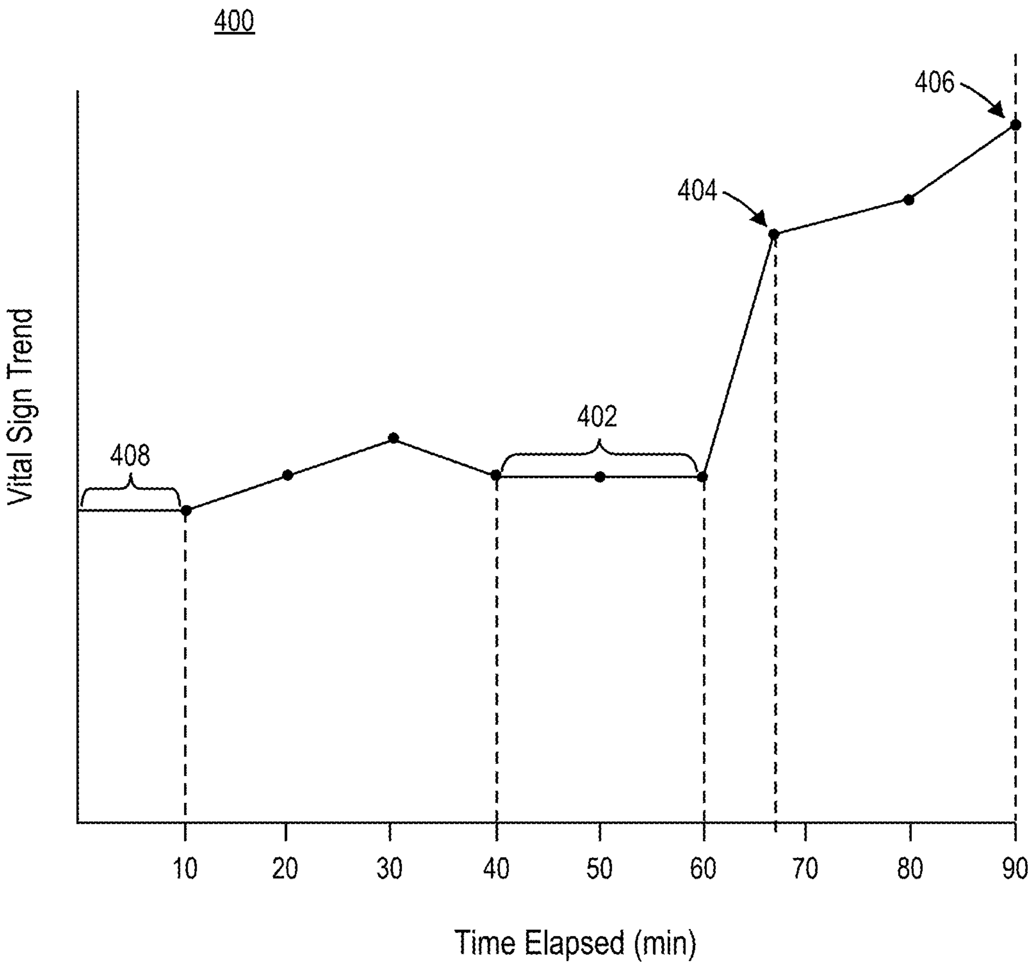
FIG. 4 depicts an exemplary chart of a vital sign trend in accordance with embodiments of the invention.

The concept of parameters for shock changing over the window in which a patient develops shock is depicted in FIG. 4. FIG. 4 illustrates an exemplary prediction window chart relating to some embodiments of the present disclosure. Chart 400 may include a trend of vital sign measurements over a period of time (such as 90 minutes, as depicted in chart 400). Over the period of time, a patient's vital sign measurements may trend upward, downward, or hold steady at various times throughout the monitoring period; however, the patient may still be diagnosed with shock at point 406 (90 minutes).

In some embodiments, the patient may experience relatively drastic changes in vital sign measurements, such as the sharp increase occurring between period 402 and point 404. Such changes may prompt a machine learning model (such as time-variant machine learning model 308) to determine that a patient is rapidly progressing to the development of shock at point 406. However, in some embodiments, the patient may still be progressing towards diagnosable shock, while the trend of a patient's vital signs is steady, as depicted in period 402. In such embodiments, while the rate of change of the vital trend line is zero, the patient may still be progressing toward a shock diagnosis. As such, time-variant machine learning model 308 may be trained by learning module 306 to change the parameters used to determine shock over time such that time-variant machine learning model 308 is able to determine the onset of shock during period 402, despite no change in vital signs.

Further, time-variant machine learning model 308 may be trained to differentiate between the steady vital sign trend of period 402 and the steady vital sign trend of period 408 such that differing parameters are used to evaluate shock despite similar vital sign measurements. For example, while period 402 and period 408 both have a slope of zero, period 408 occurs between minutes 0 and 10 of the monitoring period, while period 402 occurs between minutes 40 and 60 of the monitoring period. Thus, time-variant machine learning model 308 may be trained to associate the steady trend of period 408 with a lower probability of a patient developing shock, while time-variant machine learning model 308 may view a steady trend during period 402 as the patient's body compensating for/rallying against the impending shock. Put another way, time-variant machine learning model 308 may change the parameters used to evaluate the probability of shock based on the time period within a given monitoring period in which time-variant machine learning model 308 is determining shock.

Turning back to FIG. 3, upon being trained, time-variant machine learning model 308 may receive vital sign measurements 310 and determine shock prediction 312. Generally, the vital sign measurements 310 may be a set of features input into time-variant machine learning model 308 such that time-variant machine learning model 308 can analyze the features to determine the probability of shock occurring within a predetermined amount of time, such as within 90 minutes. In some embodiments, vital sign measurements 310 may include vital signs measured from a patient for a given time. For example, vital sign measurements 310 may include measurements for heart rate, diastolic blood pressure, systolic blood pressure, temperature, respiratory rate, and peripheral capillary oxygen saturation (SpO2). Time-variant machine learning model 308 may then determine the probability of shock developing based on vital sign measurements 310. Further, as mentioned above, time-variant machine learning model 308 may be trained to tailor the determination of the probability of shock for a particular time associated with vital sign measurements 310. As such, if time-variant machine learning model 308 receives a new set of vital sign measurements 310 10 minutes after an initial set of vital sign measurements 310, the calculus used to determine the probability of shock may be different than the calculus used by time-variant machine learning model 308 10 minutes earlier.

After analyzing vital sign measurements 310, time-variant machine learning model 308 may output shock prediction 312. In some embodiments, shock prediction 312 may be a binary yes-or-no value for whether a patient will go into shock. In such embodiments, time-variant machine learning model 308 may output a "yes" value if time-variant machine learning model 308 determines that the likelihood of shock occurring meets or exceeds a predefined threshold. For example, the predefined threshold may be 80% such that if time-variant machine learning model 308 is at least 80% likely that shock will occur, a shock prediction 312 will be a "yes" value, indicating that shock will occur for the patient.

In some embodiments, shock prediction 312 may be represented as a percentage. For example, time-variant machine learning model 308 may indicate that a user has a 75% chance of shock occurring. In some embodiments, shock prediction 312 may include a predicted time for the occurrence of shock. For example, time-variant machine learning model 308 may indicate that a patient has a 99% chance of developing shock in the next 5 minutes. Shock prediction 312 may be outputted by time-variant machine learning model 308 at any time, such as at a predetermined interval, upon receiving vital sign measurements 310, upon being prompted by a user (such as the user described in FIG. 2), and the like.

Broadly, previously received vital sign measurements 310 values and/or historic shock prediction 312 values may be stored and/or reused in order to further inform time-variant machine learning model 308 on real-life shock occurrences. In some embodiments, shock prediction 312 and/or vital sign measurements 310 associated with shock prediction 312 may be used by learning module 306 to retrain time-variant machine learning model 308. For example, information on whether or not shock occurred for a given patient, as well as the corresponding vital signs of the patient leading up to the shock occurring or not occurring, may be useful in further informing time-variant machine learning model 308 on the correlation between vital signs at a given time and shock. Doing so may result in a more robust time-variant machine learning model 308 for predicting the occurrence and/or onset of shock.

Figure 5:
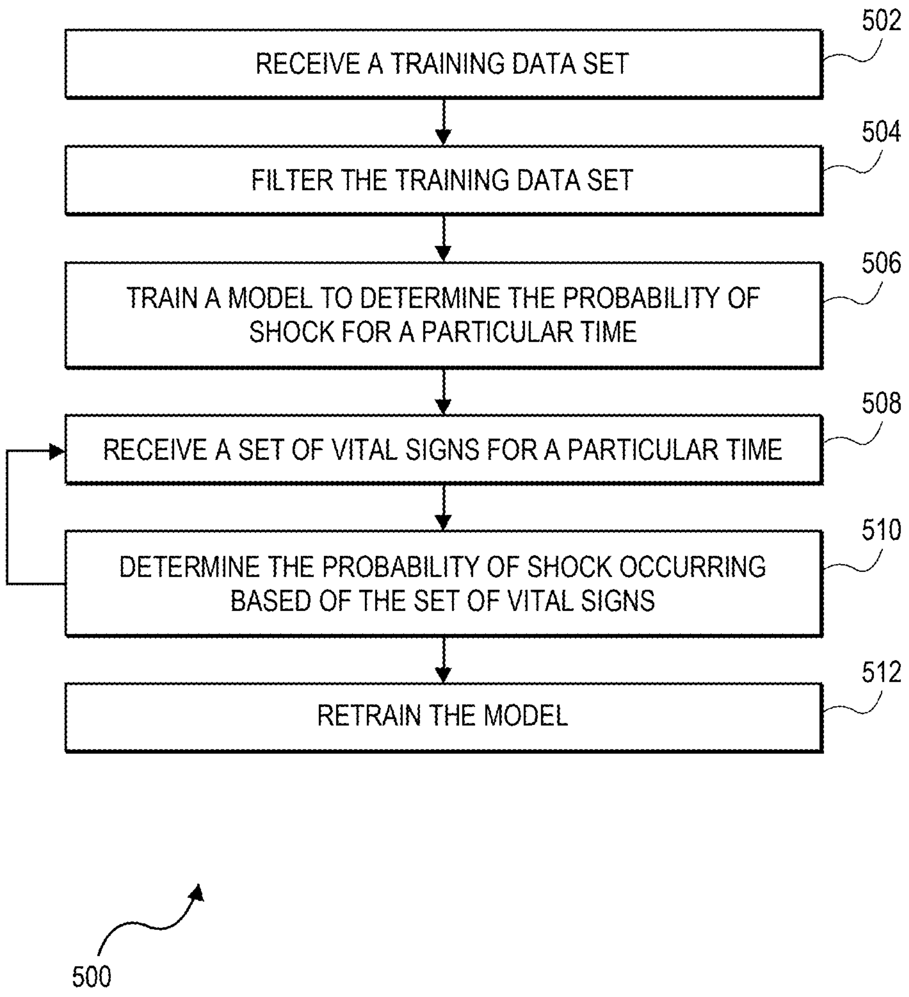
FIG. 5 depicts an exemplary flowchart for illustrating the operation of a method in accordance with embodiments of the invention.

Turning now to FIG. 5, an exemplary method of determining the probability of shock occurring is depicted and generally referred to by reference numeral 500. Method 500 may be carried out in whole or in part by any system or systems, including shock diagnosis system 200 and training system 300 described above. At step 502, a training data set is received. As described above with respect to physiological relationships 302 and vital sign training data 304 of FIG. 3, the training data set may relate to vital signs and the underlying physiological relationships that interconnect and interrelate the vital signs in the human body. For example, the training data may include measurements such as body temperature, pulse rate, respiration rate, blood pressure, and oxygen level, as well as the underlying relationships between these measurements, such as the direct relationship between heart rate and blood pressure and the fact that temperature swings paired with changes to heart rate and blood pressure are a strong indicator of shock. As discussed above, the training data may be associated with a given time relative to an initial time such that the training data may be used to determine time-specific parameters for a machine learning model.

At step 504, the training data set is filtered. As described above with respect to learning module 306 depicted in FIG. 3, the training data set may be filtered to remove spurious information that may decrease the accuracy of a machine learning model in determining the likelihood of shock occurring. Such information may include but is not limited to, data sets taken over a shorter or longer period, re-admitted patient data, data for patients who were given treatment over the monitoring period, data from patients experiencing polytrauma, and other information. In some embodiments, the training data may be filtered to tailor the training of a model to a particular subset of people and/or a subset of shock. For example, the training data may be filtered to only include data from military-aged people such that a machine learning model may be more accurately tailored for military use. For another example, the training data may be filtered to only include data from cases related to septic shock such that a machine learning model may be trained to be tailored towards septic shock.

At step 506, a model is trained to determine the probability of a patient going into shock for a particular time. As described above with respect to learning module 306 and time-variant machine learning model 308 depicted in FIG. 3, the model may be a machine learning model trained on a vital sign input data set and the underlying relationships that interconnect and interrelate vital signs. The machine learning model may use any type of machine learning model now known or later developed including but not limited to linear models, gradient-boosted models, and non-linear models.

The machine learning model may be trained to evaluate vital signs differently during various times over the monitoring period such that the model is time adaptive. For example, the underlying causal diagram of the machine learning model may alter over the course of the monitoring period. The machine learning model may alter its underlying causal diagram at a predetermined interval, such as every 5 minutes. Altering the casual diagram may account for the fact that the vital sign measurements correlating to the development of shock change over the course of a patient developing shock, as displayed by FIG. 4 (discussed above).

At step 508, a set of vital sign measurements for a particular time relative to an initial time is received. As described above with respect to body sensor 204 depicted in FIG. 2, the set of vital signs may be received from a network of sensors on a patient. The vital signs received may be any type of vital signs, including those described above with respect to FIGS. 2-3. Vital signs may be received in real time as they occur, at a predetermined interval, randomly, upon being prompted, and by any other means. The set of vital sign measurements may be from a patient in any number of settings, including, but not limited to, a hospital setting or a field setting. The set of vital sign measurements may be associated with a time or an amount of time, such as an amount of time that has elapsed since a patient began being monitored when the measurements are taken.

At step 510, the probability of shock occurring is determined based on the set of vital sign measurements. As described above with respect to FIG. 3, a model may evaluate the vital sign readings to determine how likely it is that the patient associated with the readings will develop shock, and when the patient may develop shock. In some embodiments, the model may evaluate the vital signs and the probability of shock in relation to previously measured vital signs and a previous shock probability from a previous time during the monitoring period. For example, the model may account for the fact that the model determined that a patient was 75% likely to develop shock in the next hour from a set of vital measurements taken 20 minutes ago when evaluating a new vital sign measurement set.

At step 512, the model is retrained. In some embodiments, the model is retrained based on the data received from the set of vital signs and the shock determination. For example, the model may be retrained on a shock diagnosis and the patient's vital signs for the time leading up to the patient developing shock. In some embodiments, the data may be filtered, cleansed, and analyzed prior to using the data to retrain the model. For example, if there is an intervening treatment of the patient between a first set of vital signs and a second set of vital signs, the second set of vital signs may be filtered out so as to prevent the intervening treatment from inaccurately modifying the model.

Although the present disclosure has been described with reference to the embodiments illustrated in the attached drawing figures, it is noted that equivalents may be employed and substitutions made herein without departing from the scope of the present disclosure as recited in the claims.

Having thus described various embodiments of the present disclosure, what is claimed as new and desired to be protected by Letters Patent includes the following:

1. One or more non-transitory computer-readable media comprising computer-executable instructions that, when executed by at least one processor, perform a method of determining a probability of a patient going into shock, the method comprising:

receiving, at a client device, a first set of vital sign measurements from the patient associated with a first time;

determining, using a time-variant machine learning model, the probability of the patient going into shock based on the first set of vital sign measurements, the time-variant machine learning model having a first set of parameters associated with the first time, wherein determining the probability of the patient going into shock comprises:

applying the first set of parameters to a first relationship between a first vital sign measurement and a second vital sign measurement from the first set of vital sign measurements, wherein the first vital sign measurement corresponds to a first vital sign, and the second vital sign measurement corresponds to a second vital sign, wherein the first set of parameters is selected, by the time-variant machine learning model, for application to the first relationship based on the first time;

wherein the time-variant machine learning model is trained using a training data set comprising a) historical vital sign measurements of one or more training patients over a plurality of time periods and an indication of whether or not each training patient developed shock, b) a plurality of physiological relationships between subsets of the historical vital sign measurements over the plurality of time periods, and c) a diagnosis buffer accounting for a delay in input of the historical vital sign measurements relative to the indication of training patient shock development;

receiving, at the client device, a second set of vital sign measurements from the patient associated with a second time; and updating, using the time-variant machine learning model, the probability of the patient going into shock based on the second set of vital sign measurements, the time-variant machine learning model having a second set of parameters associated with the second time, the second set of parameters differing from the first set of parameters, wherein updating the probability of the patient going into shock comprises:

applying the second set of parameters to a second relationship between a third vital sign measurement and a fourth vital sign measurement from the second set of vital sign measurements, wherein the third vital sign measurement corresponds to the first vital sign, and the fourth vital sign measurement corresponds to the second vital sign, wherein the second set of parameters is selected, by the time-variant machine learning model, for application to the second relationship based on the second time, wherein the second relationship differs from the first relationship.

2. The one or more non-transitory computer-readable media of claim 1, wherein the method further comprises:

determining, using a body sensor associated with the patient, the first set of vital sign measurements.

3. The one or more non-transitory computer-readable media of claim 2, wherein the body sensor comprises at least one of an armband, wristwatch, or chest strap.

4. The one or more non-transitory computer-readable media of claim 2, wherein determining the first set of vital sign measurements comprises:

evaluating, using a computer vision model, a set of image data associated with the patient, wherein the body sensor comprises at least one of a camera or a camcorder.

5. The one or more non-transitory computer-readable media of claim 1, wherein the method further comprises:

removing, from the training data set, spurious data associated with one or more patients determined to have experienced polytrauma.

6. The one or more non-transitory computer-readable media of claim 1, wherein the time-variant machine learning model is operable to modify an operating set of parameters at a predetermined interval, wherein the first set of parameters is the operating set of parameters at the first time, and the second set of parameters is the operating set of parameters at the second time.

7. The one or more non-transitory computer-readable media of claim 1, wherein the time-variant machine learning model is trained using the training data set cleansed to remove at least one of duplicate data, polytrauma patient data, or re-admitted patient data.

8. A method for determining a probability of a patient going into shock, the method comprising:

receiving, at a client device, a first set of vital sign measurements from the patient associated with a first time;

determining, using a time-variant machine learning model, the probability that the patient will go into shock within a predetermined time period based on the first set of vital sign measurements, the time-variant machine learning model having a first set of parameters associated with the first time, wherein determining the probability of the patient going into shock comprises:

applying the first set of parameters to a first relationship between a first vital sign measurement and a second vital sign measurement from the first set of vital sign measurements, wherein the first vital sign measurement corresponds to a first vital sign, and the second vital sign measurement corresponds to a second vital sign, wherein the first set of parameters is selected, by the time-variant machine learning model, for application to the first relationship based on the first time;

wherein the time-variant machine learning model is trained using a training data set comprising a) historical vital sign measurements of one or more training patients over a plurality of time periods and an indication of whether or not each training patient developed shock, b) a plurality of physiological relationships between subsets of the historical vital sign measurements over the plurality of time periods, and c) a diagnosis buffer accounting for a delay in input of the historical vital sign measurements relative to the indication of training patient shock development;

receiving, at the client device, a second set of vital sign measurements from the patient associated with a second time;

updating, using the time-variant machine learning model, the probability that the patient will go into shock within the predetermined time period based on the first set of vital sign measurements and the second set of vital sign measurements, the time-variant machine learning model having a second set of parameters associated with the second time, the second set of parameters differing from the first set of parameters;

receiving, at the client device, a third set of vital sign measurements from the patient associated with a third time; and updating, using the time-variant machine learning model, the probability that the patient will go into shock within the predetermined time period based on the first set of vital sign measurements, the second set of vital sign measurements, and the third set of vital sign measurements, the time-variant machine learning model having a third set of parameters associated with the third time, the third set of parameters differing from the first set of parameters and the second set of parameters, wherein updating the probability of the patient going into shock comprises:

applying the second set of parameters to a second relationship between a third vital sign measurement and a fourth vital sign measurement from the second set of vital sign measurements, wherein the third vital sign measurement corresponds to the first vital sign, and the fourth vital sign measurement corresponds to the second vital sign, wherein the second set of parameters is selected, by the time-variant machine learning model, for application to the second relationship based on the second time, wherein the second relationship differs from the first relationship.

9. The method of claim 8, further comprising:

measuring the first set of vital sign measurements associated with the patient, comprising:

capturing a set of image data associated with the patient using a recording device; and determining, by inputting the set of image data into a computer vision model, the first set of vital sign measurements.

10. The method of claim 8, wherein the first time and the second time are relative to an initial time, the initial time being a beginning of a monitoring period of the patient.

11. The method of claim 8, wherein the first set of parameters is determined based on a subset of training data associated with a delay time, the delay time relative to a length of time since a historical monitoring period began.

12. The method of claim 8, wherein the predetermined time period is 90 minutes.

13. The method of claim 8, wherein the first set of vital sign measurements and the second set of vital sign measurements each comprise a heart rate measurement, a diastolic blood pressure measurement, a systolic blood pressure measurement, a temperature measurement, a respiratory rate measurement, and a peripheral capillary oxygen saturation (SpO2) measurement.

14. A system for determining a probability of a patient going into shock, the system comprising:

a body sensor for measuring a plurality of vital sign measurements associated with the patient;

a time-variable machine learning model for determining the probability of the patient going into shock; and one or more non-transitory computer-readable media comprising computer-executable instructions that, when executed by at least one processor, perform a method of determining the probability of the patient going into shock, the method comprising:

receiving a first set of vital sign measurements from the plurality of vital sign measurements associated with a first time;

determining, using a time-variant machine learning model, the probability of the patient going into shock based on the first set of vital sign measurements, the time-variant machine learning model having a first set of parameters associated with the first time, wherein determining the probability of the patient going into shock comprises:

applying the first set of parameters to a first relationship between a first vital sign measurement and a second vital sign measurement from the first set of vital sign measurements, wherein the first vital sign measurement corresponds to a first vital sign, and the second vital sign measurement corresponds to a second vital sign, wherein the first set of parameters is selected, by the time-variant machine learning model, for application to the first relationship based on the first time;

wherein the time-variant machine learning model is trained using a training data set comprising a) historical vital sign measurements of one or more training patients over a plurality of time periods and an indication of whether or not each training patient developed shock, b) a plurality of physiological relationships between subsets of the historical vital sign measurements over the plurality of time periods, and c) a diagnosis buffer accounting for a delay in input of the historical vital sign measurements relative to the indication of training patient shock development;

receiving a second set of vital sign measurements from the plurality of vital sign measurements associated with a second time; and updating, using the time-variant machine learning model, the probability of the patient going into shock based on the second set of vital sign measurements, the time-variant machine learning model having a second set of parameters associated with the second time, the second set of parameters differing from the first set of parameters, wherein updating the probability of the patient going into shock comprises:

applying the second set of parameters to a second relationship between a third vital sign measurement and a fourth vital sign measurement from the second set of vital sign measurements, wherein the third vital sign measurement corresponds to the first vital sign, and the fourth vital sign measurement corresponds to the second vital sign, wherein the second set of parameters is selected, by the time-variant machine learning model, for application to the second relationship based on the second time, wherein the second relationship differs from the first relationship.

15. The system of claim 14, wherein the time-variant machine learning model is trained to determine the probability of shock for the patient when the patient is in an austere environment.

16. The system of claim 14, wherein the method further comprises:

storing the first set of vital sign measurements and the probability of shock occurring for retraining the time-variant machine learning model.

17. The system of claim 14, wherein the body sensor is attached to the patient and transmits signals to a client device associated with a user, the client device running the time-variant machine learning model.

18. The system of claim 14, wherein the time-variant machine learning model is agnostic to shock types such that the time-variant machine learning model determines the probability of a plurality of shock types occurring.

19. The system of claim 14, further comprising:

a client device configured to present a set of vital sign measurements associated with the patient and the probability of the patient going into shock to a user, wherein the probability of the patient going into shock is presented to the user when the probability exceeds a predetermined threshold.

* * * * *